(12) United States Patent
Nomoto et al.

(10) Patent No.: US 9,463,120 B2
(45) Date of Patent: Oct. 11, 2016

(54) ABSORBENT ARTICLE CONTAINER

(75) Inventors: Sekai Nomoto, Kagawa (JP); Yukiko Matsumura, Kagawa (JP); Sachi Hamada, Kagawa (JP)

(73) Assignee: Unicharm Corporation, Ehime (JP)

( * ) Notice: Subject to any disclaimer, the term of this patent is extended or adjusted under 35 U.S.C. 154(b) by 230 days.

(21) Appl. No.: 14/118,726

(22) PCT Filed: May 15, 2012

(86) PCT No.: PCT/JP2012/062342
§ 371 (c)(1),
(2), (4) Date: Feb. 25, 2014

(87) PCT Pub. No.: WO2012/157620
PCT Pub. Date: Nov. 22, 2012

(65) Prior Publication Data
US 2014/0367290 A1    Dec. 18, 2014

(30) Foreign Application Priority Data

May 19, 2011 (JP) .................................. 2011-112926
Mar. 22, 2012 (JP) .................................. 2012-065222

(51) Int. Cl.
*A61B 17/06* (2006.01)
*A61B 19/02* (2006.01)
(Continued)

(52) U.S. Cl.
CPC ....... *A61F 13/5514* (2013.01); *A61F 13/4704* (2013.01); *A61F 13/55145* (2013.01); *A61F 2013/8497* (2013.01)

(58) Field of Classification Search
CPC ............. A61F 15/001; A61F 13/5513; A61F 13/5514; A61F 13/55145; A61F 13/4704; A61F 2013/8497

USPC ........... 206/440, 438, 494, 812, 457, 459.1, 206/459.5
See application file for complete search history.

(56) References Cited

U.S. PATENT DOCUMENTS

2007/0108078 A1* 5/2007 Molina ................. A61F 13/551 206/438
2007/0267322 A1* 11/2007 Kishida ................. A61F 13/551 206/776

FOREIGN PATENT DOCUMENTS

JP     2000-513306 A     10/2000
JP     2004-537474 A     12/2004
(Continued)

OTHER PUBLICATIONS

Japanese Office Action and English translation from corresponding Japanese application No. 2012-065222 dated Aug. 11, 2015 (3 pgs).
(Continued)

*Primary Examiner* — Jacob K Ackun
*Assistant Examiner* — Rafael Ortiz
(74) *Attorney, Agent, or Firm* — Brinks Gilson & Lione

(57) ABSTRACT

In the absorbent article package, display element unit that has display elements exhibiting a pattern and/or a mark and non-display element unit that does not have display elements are provided on a package sheet that encloses the absorbent article. A window unit, which is configured to allow the absorbent article packages contained therein to be seen, is formed on one side of a container bag and is configured so that only the non-display element unit can be seen through the window. A container bag display unit that shows the display elements is provided on the one side where the container bag window is provided.

20 Claims, 10 Drawing Sheets

(51) Int. Cl.
  *A61L 15/00* (2006.01)
  *A61F 13/551* (2006.01)
  *A61F 13/47* (2006.01)
  *A61F 13/84* (2006.01)

(56) References Cited

FOREIGN PATENT DOCUMENTS

| | | |
|---|---|---|
| JP | 2006-526550 A | 11/2006 |
| JP | 2008-507385 A | 3/2008 |
| JP | 2008-528398 A | 7/2008 |
| JP | 2009-518248 | 5/2009 |
| JP | 2010-540366 A | 12/2010 |
| WO | WO 2006/015206 A2 | 2/2006 |

OTHER PUBLICATIONS

International Search Report based on corresponding PCT application No. PCT/JP2012/062342 dated Aug. 14, 2012 (4 pgs).
Chinese Office Action and English translation from corresponding Chinese application No. 201280024183.x dated Jun. 30, 2015 (12 pgs).
Japanese Office Action and English translation from corresponding Japanese Application No. 2012-065222 dated Nov. 4, 2015 (4 pgs).

* cited by examiner

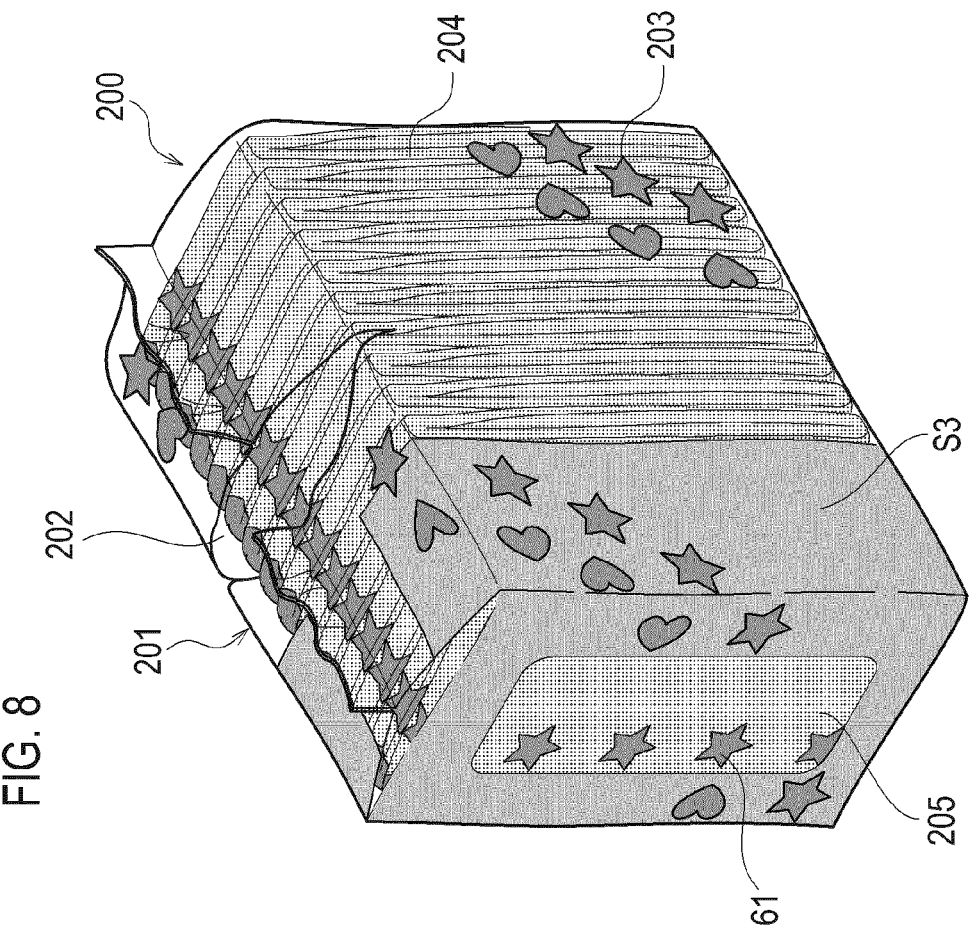
FIG. 8
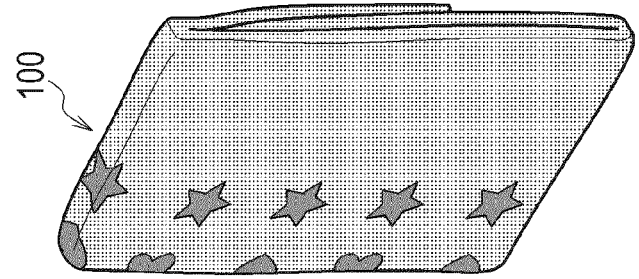

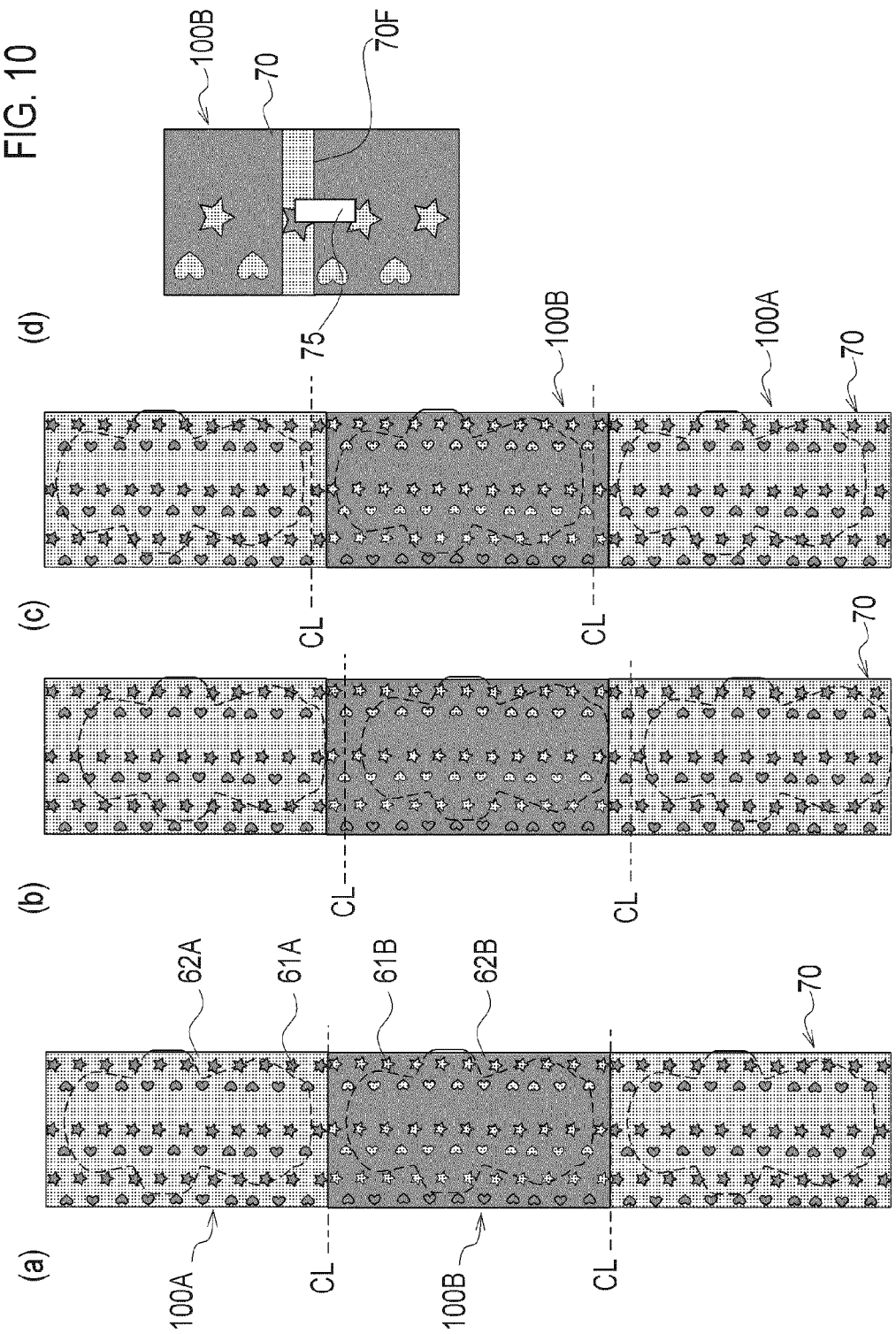

ABSORBENT ARTICLE CONTAINER

RELATED APPLICATION

This application is a 35 U.S.C. §371 national phase filing of International Patent Application No. PCT/JP2012/062342, filed May 15, 2012, through which and to which priority is claimed under 35 U.S.C. §119 to Japanese Patent Application Nos. 2011-112926, filed May 19, 2011 and 2012-065222, filed Mar. 22, 2012.

TECHNICAL FIELD

The present invention relates to an absorbent article container that contains a plurality of absorbent article packages in which an absorbent article such as a sanitary napkin is individually packaged.

BACKGROUND ART

Patent Literature 1 discloses an absorbent article container that has a container bag having contained an absorbent article package in which an absorbent article is individually packaged by a package sheet, and is configured such that patterns indicating a characteristic and the like of the absorbent article are imparted to the package sheet, a window is formed through the container bag, and the patterns of the absorbent article package are visible through the window.

According to the aforementioned absorbent article container, since the patterns are imparted to the package sheet, it is possible to improve a decoration property. Moreover, according to the absorbent article container, a user is able to see the patterns of the package sheet through the window from the outer side of the container bag, and to understand a characteristic or usage such as the performance of the absorbent article.

CITATION LIST

Patent Literature

[PTL 1] Japanese Unexamined Patent Publication No. 2008-528398 (FIG. 1, Paragraph [0045] and [0046], and the like)

SUMMARY OF INVENTION

However, the aforementioned absorbent article container has the following problems. The absorbent article container contains a plurality of absorbent article packages and is configured such that a part of the absorbent article packages is visible through the window. For example, as illustrated in FIG. 1 of Patent Literature 1, when the patterns are imparted to a thickness part of the absorbent article, a pattern visible through the window is smaller relative to the size of an entire container. Accordingly, since a user is not able to apparently recognize the patterns in the state in which the absorbent article package is contained in the container bag, it may be difficult to understand the characteristic and the like of the absorbent article.

Furthermore, in addition to the patterns of the absorbent article packages, it is considered imparting characters indicating the characteristic and the like of the absorbent articles to the container bag. However, if the characters are overlapped and imparted to the window in the aforementioned absorbent article container, it is probable that visibility of the characters is reduced because the patterns imparted to the package sheet overlap the characters.

Therefore, the present invention has been achieved in view of the above-described circumstances, and an object thereof is to provide an absorbent article container capable of improving the decoration property of an absorbent article package, and allowing a user to easily understand a characteristic or usage of the absorbent article in the state in which a plurality of absorbent article packages are contained in the container.

In order to resolve the above-described problems, there is provided an absorbent article container including an absorbent article having a liquid-permeable topsheet, a liquid-impermeable backsheet, and an absorber arranged between the topsheet and the backsheet, a package sheet that individually packages the absorbent article, an absorbent article package in which the package sheet and the absorbent article are folded in a state in which the absorbent article has been arranged on the package sheet and the absorbent article is individually packaged by the package sheet, and a container bag that contains a plurality of absorbent article packages, wherein the package sheet is provided with a display element unit having a display element indicating a pattern and/or a mark and a non-display element unit having no display element, the container bag is provided with a window unit through which the absorbent article package contained in the container bag is visible, only the non-display element unit of the package sheet is configured to be visible through the window unit, and a container bag display unit indicating the display element is provided on a surface on which the window unit of the container bag has been provided.

BRIEF DESCRIPTION OF DRAWINGS

FIG. 8 is a perspective view of an absorbent article container according to the embodiment.

FIG. 10 is a diagram schematically illustrating manufacturing steps of an absorbent article package according to the modification.

DESCRIPTION OF EMBODIMENTS

Figure 1:
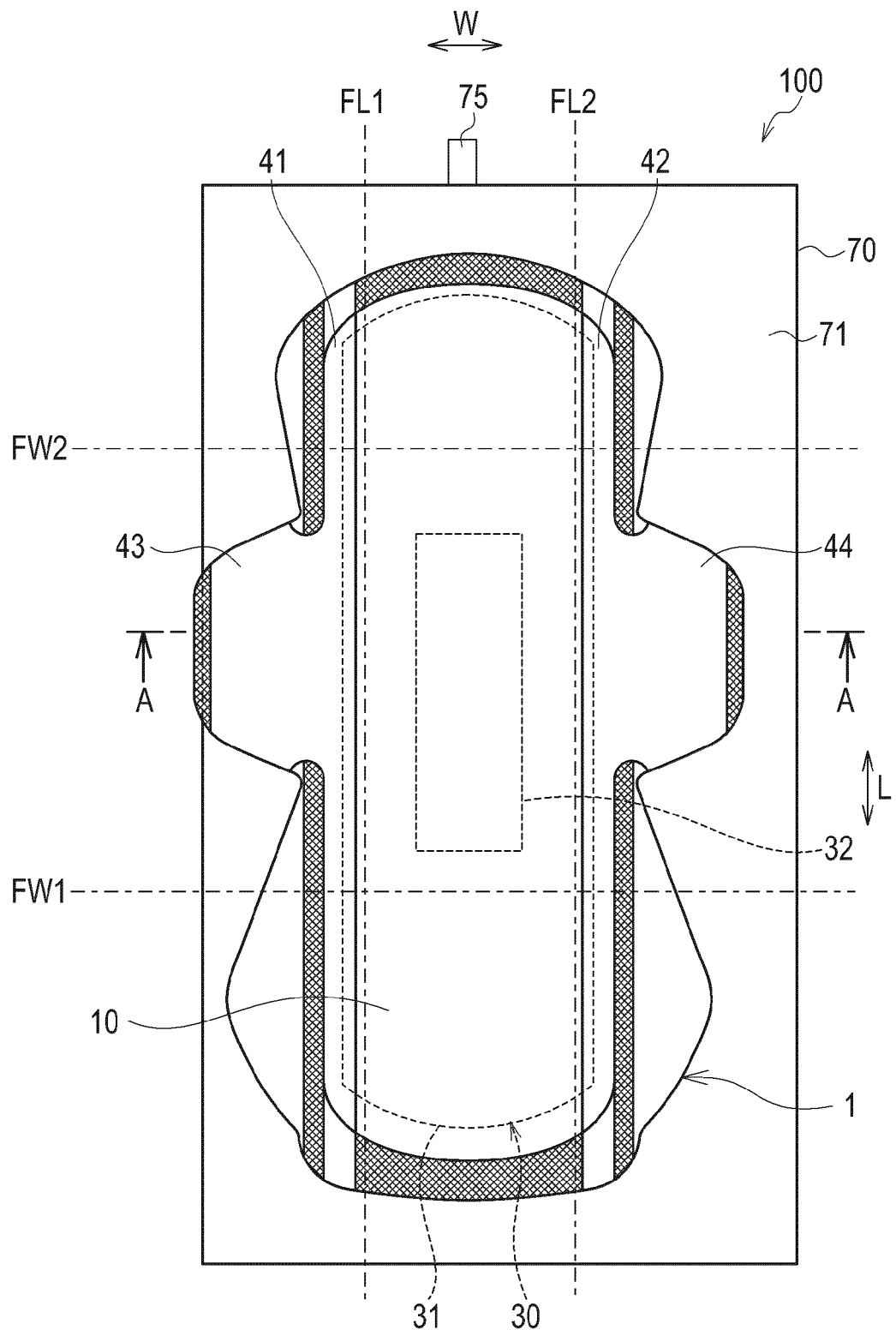
FIG. 1 is a plan view when viewed from a skin contact surface side of an absorbent article package according to an embodiment.
Figure 2:
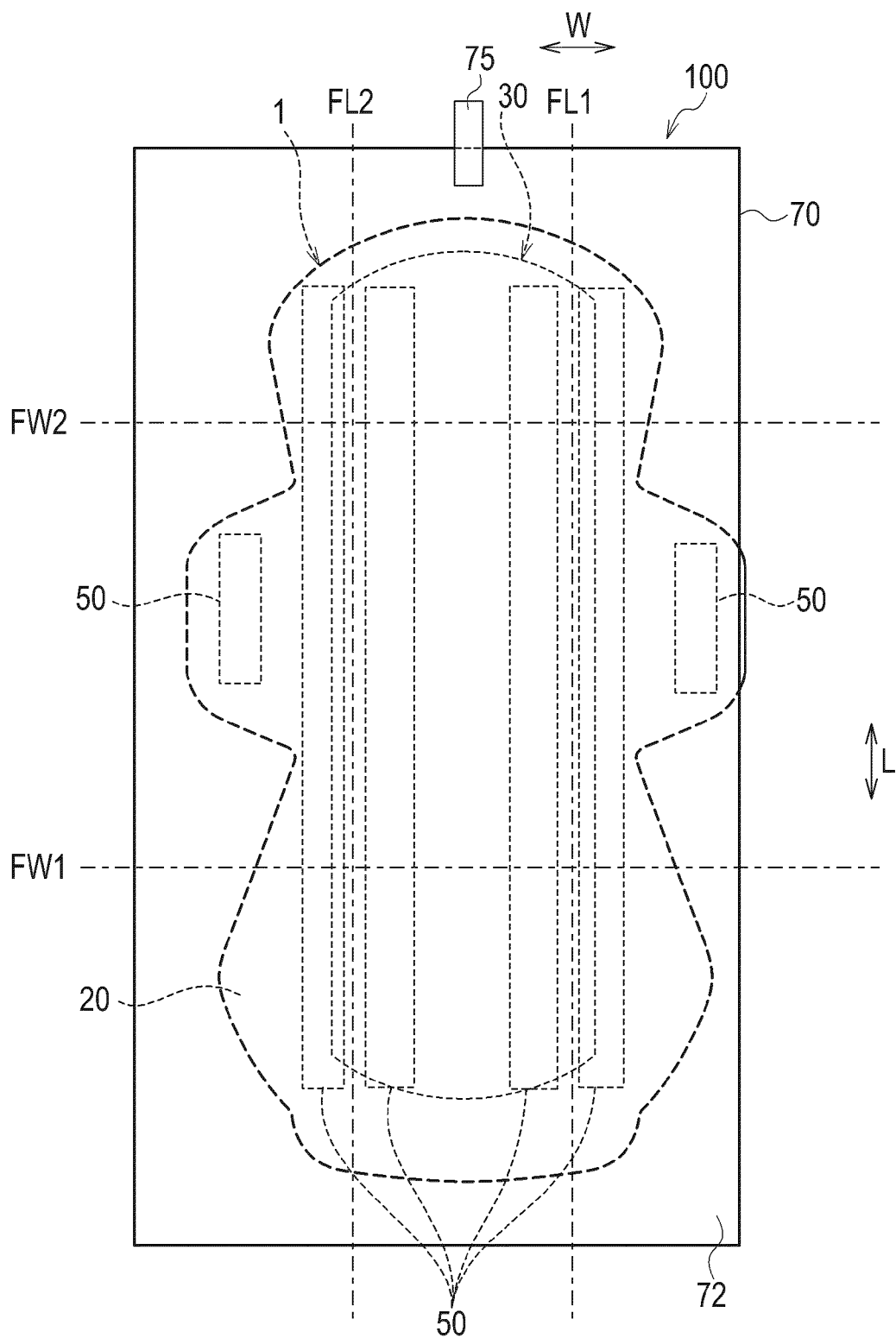
FIG. 2 is a rear view when viewed from a non-skin contact surface side of the absorbent article package illustrated in FIG. 1.
Figure 3:
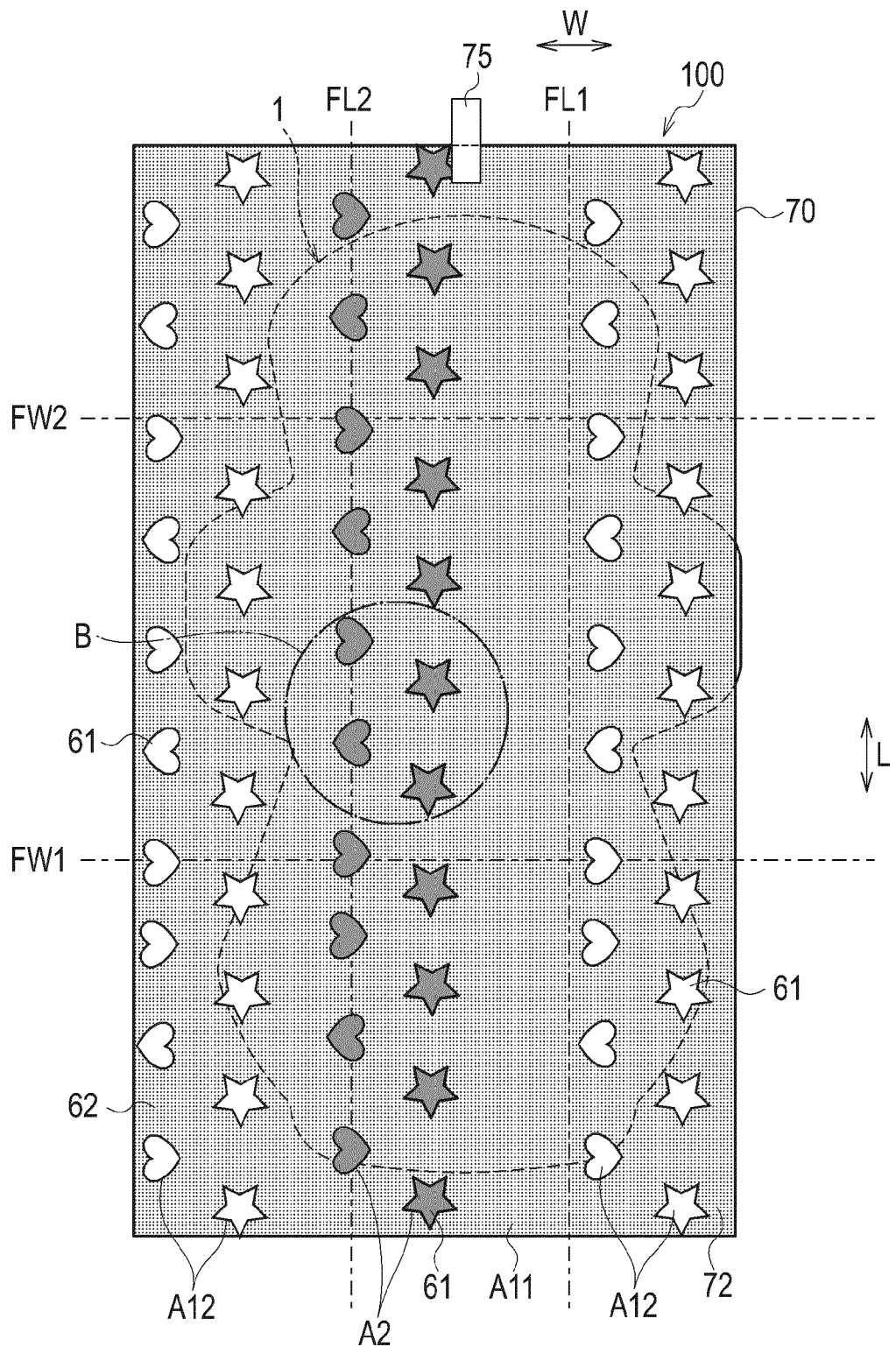
FIG. 3 is a rear view when viewed from the non-skin contact surface side of the absorbent article package illustrated in FIG. 1.
Figure 4:
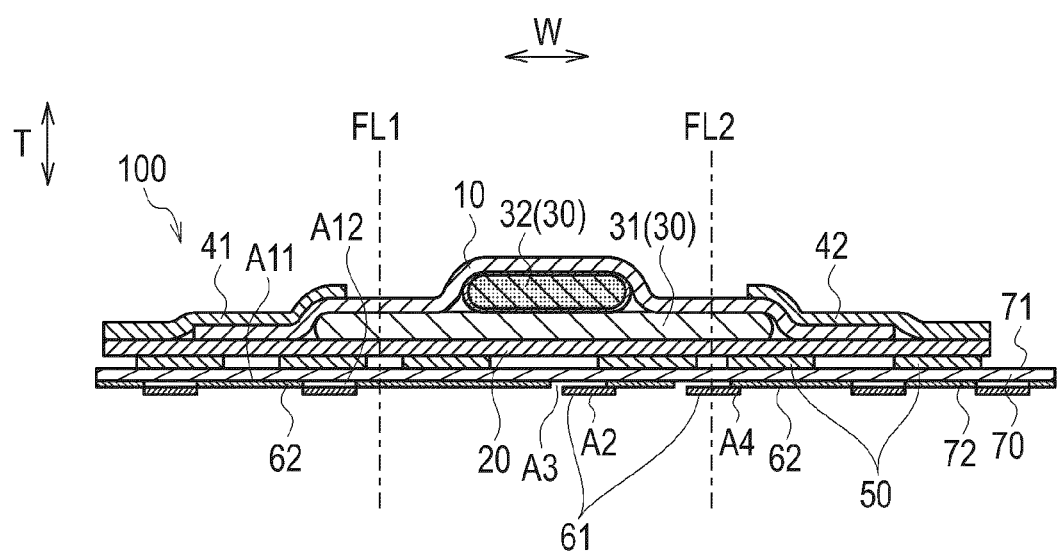
FIG. 4 is a sectional view taken along line A-A illustrated in FIG. 1.

With reference to FIG. 1 to FIG. 4, an absorbent article package according to an embodiment will be described. FIG. 1 is a plan view of the absorbent article package, and FIG. 2 and FIG. 3 are rear views of the absorbent article package. FIG. 2 illustrates the state in which printing of a package sheet is omitted, which will be described later, and FIG. 3 illustrates the printing of the package sheet. FIG. 4 is a sectional view taken along line A-A illustrated in FIG. 1. As illustrated in FIG. 1 to FIG. 4, an absorbent article package 100 includes an absorbent article 1, and a package sheet 70 that individually packages the absorbent article 1. The absorbent article 1 according to the present embodiment is a sanitary napkin, for example.

The absorbent article package 100 is configured such that the package sheet 70 and the absorbent article 1 are folded in the state in which the absorbent article 1 is arranged on the package sheet 70, and then the absorbent article 1 is individually packaged. FIG. 1 to FIG. 3 illustrate the state in which the absorbent article 1 is individually packaged by the package sheet 70 and then the absorbent article 1 is opened.

The absorbent article 1 has a topsheet 10 that is in contact with the skin of the wearer, a liquid-impermeable backsheet 20 that does not allow liquid to pass through, and an absorber 30. The absorber 30 is arranged between the top sheet 10 and the backsheet 20. Consequently, the absorber 30 is indicated by a broken line in FIG. 1 and the like. The absorber 30 is arranged in the central part in a longitudinal direction L and a widthwise direction W of the absorbent article 1. Furthermore, in the plan view illustrated in FIG. 1, the absorbent article 1 has the absorber 30, and includes an absorbent body extending in the longitudinal direction L, and wing units 43 and 44 provided at the outer side of the absorbent body in the widthwise direction W perpendicular to the longitudinal direction L. Additionally, the absorbent article 1 includes sidesheets 41 and 42 provided at the outer side of the absorber 30 in the widthwise direction W.

The topsheet 10 is a liquid-permeable sheet that allows liquids such as bodily fluid to pass through. The topsheet 10 covers at least the surface of the absorber 30. The topsheet 10 is not particularly limited as long as the topsheet 10 is a sheet-like material having a structure that allows the liquids to pass through, such as a nonwoven fabric, a woven fabric, a perforated plastic sheet, and a mesh sheet. Both natural fibers and chemical fibers can be used as a woven and nonwoven fabric.

Examples of the natural fibers include cellulose such as ground pulp and cotton. Examples of the chemical fibers include regenerated cellulose such as rayon and fibril rayon; semi-synthetic cellulose such as acetate and triacetate; thermoplastic hydrophobic chemical fibers; and thermoplastic hydrophobic chemical fibers that have been subjected to hydrophilic treatment. Examples of the thermoplastic hydrophobic chemical fibers include monofilament fibers such as polyethylene (PE), polypropylene (PP), and polyethylene phthalate (PET); fibers obtained by graft polymerization of polyethylene and polypropylene; and composite fibers with core-clad structures.

Furthermore, the topsheet 10 according to the present embodiment can be made from one or more materials. For example, the topsheet 10 may include a woven cloth, a nonwoven cloth, a polymer film, a film nonwoven laminate and the like, and a combination thereof. The nonwoven cloth includes an air-laid nonwoven web, a spun bond nonwoven web, a melt blown nonwoven web, a bonded carded web, a hydraulically entangled nonwoven web, a spun lace web and the like, and a combination thereof. The nonwoven cloth is formed by one of a dry type (such as a card method, a spun bond method, a melt blown method, and an air-laid method) and a wet type.

The nonwoven cloth may be formed by combining a plurality of methods of the dry type method and the wet type method with each other. Furthermore, it is possible to exemplify a method such as thermal bonding, needle punch, or chemical bonding. In addition, a method for manufacturing the nonwoven cloth is not limited to the aforementioned method. An example of another preferred material may include rayon, polyester, polypropylene, polyethylene, nylon, a fine perforated film web that is another thermally bondable fiber, a mesh-like member, and a bonded carded web that is a combination thereof. These webs, for example, can be prepared from polyolefin such as polypropylene, polyethylene, or copolymer thereof, general polylactate, nylon, or a polymer material such as polyester including another thermally bondable aliphatic ester.

The backsheet 20 has substantially the same length as the length of the topsheet 10. The backsheet 20 may use a polymer film, a woven cloth, a nonwoven cloth and the like, a combination or a constituent material thereof, and the like. The polymer film may be composed of polyethylene, polypropylene, polyester and the like, and a combination thereof. Moreover, the polymer film can be micro-embossed to have a printed design or a printed message to a consumer, and/or can be at least partially colored. Preferably, the backsheet may be an air-permeable microporous film. Furthermore, it is preferable that the backsheet 20 is made from a material having flexibility to the extent that a user does not feel discomfort when wearing the absorbent article 1.

The absorber 30 includes hydrophilic fibers and pulp. The absorber 30 includes a lower layer absorber 31 and an upper layer absorber 32 stacked on the lower layer absorber 31. The upper layer absorber 32 is smaller than the lower layer absorber 31 in the longitudinal direction L and the widthwise direction W. In addition, the lower layer absorber 31 and the upper layer absorber 32 may be provided separately from each other, or may be integrally formed with each other. Furthermore, the lower layer absorber 31 and the upper layer absorber 32 are bonded by a hot melt type adhesive.

The absorber 30 including the lower layer absorber 31 and the upper layer absorber 32 is formed by a material capable of absorbing bodily fluid such as menstrual blood. A material suitable for the absorber 30, for example, includes cellulose, wood pulp fluff, rayon, cotton, and melt blown polymer such as polyester, polypropylene, or coform. The absorber 30 may be formed by stacking hydrophilic fibers or powder by an air-laid method, may be an air-laid sheet obtained by forming hydrophilic fibers or powder in a sheet shape by an air-laid method, or may be formed by arranging ground pulp mixed with high absorbent polymer on a tissue (for example, a basis weight 15 $g/m^2$) and surrounding the ground pulp with the tissue.

The sidesheets 41 and 42 can be selected from a similar material to that of the topsheet 10. However, in order to prevent menstrual blood from being leaked to the widthwise outer side of the absorbent article 1, it is preferable that the sidesheets 41 and 42 have hydrophobic property or water-repellent property. Specifically, a spun bond nonwoven cloth, an SMS nonwoven cloth and the like are exemplified. The sidesheet constitutes a contact surface with a skin. Therefore, in order to reduce friction stimulation to a skin, it is preferable to use an air-through nonwoven cloth.

The sidesheets 41 and 42 are located on both sides of the topsheet 10. The sidesheets 41 and 42 cover a part of the side edges of the absorber 30, and the wing units 43 and 44. In the absorbent article 1, the peripheries of the topsheet 10, the sidesheets 41 and 42, and the backsheet 20 are joined, and the absorber 30 is included within. As a method for joining the topsheet 10 to the backsheet 20, it is possible to use one of heat embossing, ultrasonic wave, and a hot melt type adhesive, or a combination of a plurality thereof.

In the backsheet 20, an adhesive member 50 is applied on the surface coming into contact with underwear (see FIG. 2). The adhesive member 50 is formed by applying an adhesive on the non-skin contact surface of the backsheet 20, or applying an adhesive on the package sheet 70, the entire surface of which is stripped, and then transferring the adhesive on the non-skin contact surface of the backsheet 20. A plurality of adhesives 50 are arranged in a stripe shape extending in the longitudinal direction L at the widthwise center of the absorbent article.

The adhesive member 50 is also provided on the surfaces coming into contact with underwear at the wing unit 43 and the wing unit 44. In a state before being used, the adhesive member 50 comes into contact with the package sheet 70, and the adhesive member is prevented from deteriorating by the package sheet 70 before being used. At the time of use, the package sheet 70 is stripped by a wearer. In addition, it may be configured such that the deterioration of the adhesive member is prevented by a release sheet including a paper, other than the package sheet 70, before being used. In addition, the adhesive member, for example, may use a hot melt type adhesive.

The package sheet 70 individually packages the absorbent article 1. The package sheet 70 includes a rear surface 71 that is an opposite surface facing the absorbent article 1 at the side of the backsheet 20 of the absorbent article 1, and a front surface 72 that is a non-opposite surface not facing the absorbent article 1 and is positioned at the outer side in the state in which the absorbent article 1 is contained.

The material of the package sheet 70 is not particularly limited, and for example, includes various films, such as a plastic film of polyethylene, polypropylene, polyester and the like, or a nylon film, an air permeable film in which a filler such as barium sulfate is added and stretched, and a film obtained by laminating nonwoven cloths. The basis weight of the package sheet 70 is 10 g/m² to 50 g/m², and preferably, is 12 g/m² to 30 g/m².

Moreover, the rear surface of the package sheet 70 is subject to a process capable of stripping the adhesive member without reducing the adhesibility of the adhesive member. A processing method capable of stripping the adhesive member includes a method for applying a stripping agent on the entire surface (to be processed) of the package sheet 70 and heating and drying the stripping agent, a method for spraying a stripping agent on the entire surface (to be processed) of the rear surface of the package sheet 70 by using a spray and forming a thin film, and the like. Examples of the stripping agent include silicon-based resin, fluorine-based resin, and octaldecyl isocyanate-based resin.

Figure 5:
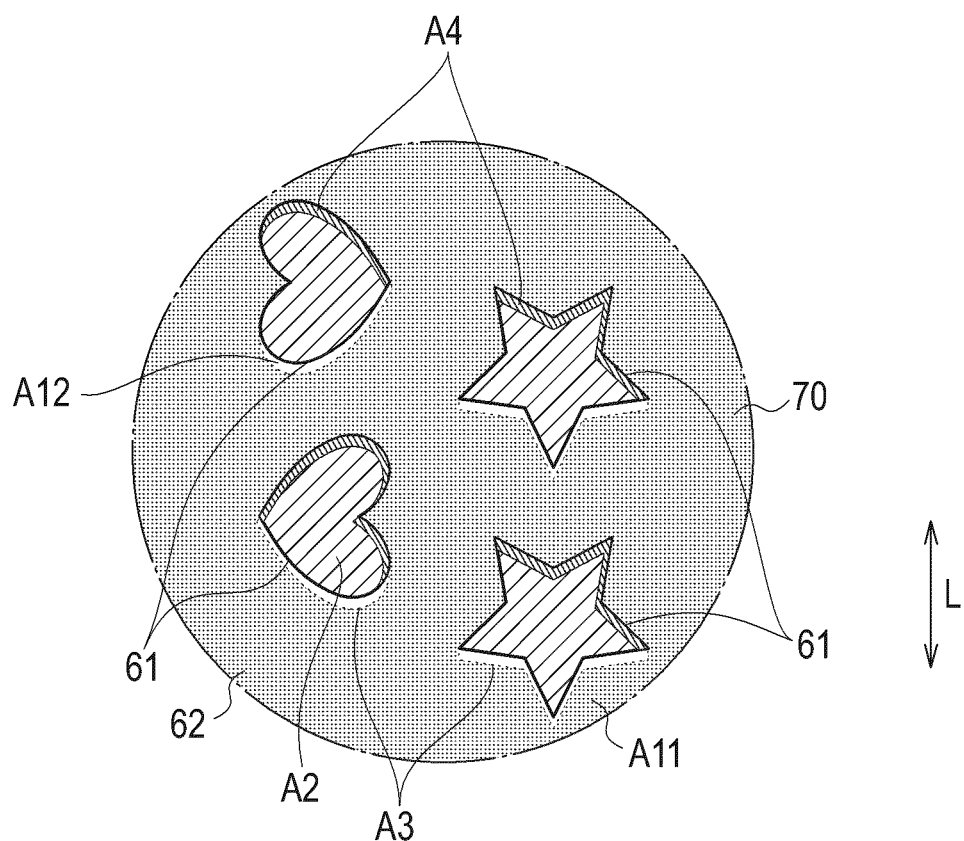
FIG. 5 is a partially exploded view of a part B of FIG. 3.

The front surface 72 of the package sheet 70 is a surface positioned at the outer side when the absorbent article 1 is packaged by the package sheet 70, and is a surface seen in FIG. 2 and FIG. 3. The front surface 72 of the package sheet 70 is subject to printing. FIG. 5 is a partially exploded view of a part B of FIG. 3. The package sheet 70 is provided with a first colored area A11 colored with a first color, a first non-colored area A12 not colored with the first color, a second colored area A2 colored with a second color, a non-colored area A3 colored with neither the first color nor the second color, and a superposition area A4 colored with both the first color and colored with the second color.

The first colored area A11 is provided in the whole of the package sheet 70, and constitutes a non-display element unit 62 that is a background of display element units 61 including patterns. The non-display element unit 62 is a part other than display elements having patterns or characters. The first non-colored area A12 constitutes the display element unit 61 indicating a star-shaped pattern and a heart-shaped pattern. The second colored area A2 is printed with the second color different from the first color. The second colored area A2 constitutes the display element unit 61 indicating a star-shaped pattern and a heart-shaped pattern. The first non-colored area A12 and the second colored area A2 have the same shape and are arranged to partially overlap with each other.

The display element unit 61 is configured to indicate the display elements including the patterns or the characters, and is able to indicate a characteristic or usage such as the performance of the absorbent article 1. A wearer is able to understand the performance and the like of the absorbent article 1 from the outer side of the package sheet 70 at the time of selection of the absorbent article 1 or at the time of use of the absorbent article 1. In addition, it may be configured such that the performance and the like of the absorbent article are indicated on the basis of the content (the image or meaning of patterns) of the display elements of the display element units 61, or the performance and the like of the absorbent article are indicated on the basis of the content and colors of the display elements.

As described above, since it is configured such that the package sheet is decorated by patterns or colors and the performance and the like of the absorbent article are indicated by the decoration, even when the absorbent article 1 is kept after being extracted from a container bag 201 (see FIG. 8) which will be described later or the absorbent article 1 is carried after being extracted from the container bag 201, a wearer is able to see the display elements of the package sheet 70 to understand and select the absorption performance of the absorbent article 1, such as whether it is an absorbent article in daytime, in the state in which the absorbent article 1 is surrounded by the package sheet 70. Furthermore, as compared with the case of indicating the absorbent article 1 by characters and the like, since it is not possible to know that it is a sanitary napkin at first glance, it is preferable in the case in which the content is not desired to be recognized.

At the vicinity of the second colored area A2, the non-colored area A3 and the superposition area A4 are provided. The non-colored area A3 is a non-colored area in which the color of the package sheet 70 itself is shown. The non-colored area A3 is arranged along the outline of the second colored area A2. The superposition area A4 is an area, in which the first color and the second color overlap each other, and is deeper than the first color and the second color.

As described above, the non-colored area A3 is arranged along the outline of the second colored area A2, so that the first colored area A11 and the second colored area A2 can be seen to stand out by color contrast between the colored first colored area A11 and second colored area A2, and the non-colored area A3, and it is possible to three-dimensionally express the display elements in a pseudo manner. Furthermore, the superposition area A4 is arranged along the outline of the second colored area A2, so that the outline of the second colored area A2 can be made deeper, and the display elements can be shown as if they are three-dimensionally formed through light and shade by the color contrast.

The display elements are three-dimensionally expressed to improve the feeling of the package sheet 70 itself, so that it is possible to allow the absorbent article package 100 to be seen as fabric such as a handkerchief in a packaged state. Furthermore, no embossing for three-dimensional decoration is performed for the package sheet itself and the display elements are three-dimensionally expressed by the color contrast, so that it is possible to suppress the occurrence of a problem due to stripping of an adhesive member and the like.

As illustrated in FIG. 3, the first non-colored areas A12 are provided at the center, in the widthwise direction W, of the absorbent article 1 and both ends, in the widthwise direction W, of the absorbent article 1. The second colored areas A2 are arranged to partially overlap the first non-colored area A12 positioned at the center in the widthwise direction W and are not arranged to overlap the first non-colored area A12 positioned at both ends in the widthwise direction W. That is, the first non-colored area A12 positioned at both widthwise ends is not colored with the second color and becomes the non-colored area A3. The first non-colored area A12 positioned at the widthwise center and the first non-colored area A12 positioned at both widthwise ends show different aspects. Accordingly, it is possible to allow decoration patters of a plurality of first non-colored areas to be different from each other, resulting in the improvement of decoration property.

The superposition area A4 and the first non-colored area A12 are arranged to be interposed between the second colored areas A2 in the longitudinal direction L. The superposition area A4 and the non-colored area A3 are arranged at both ends, in the longitudinal direction L, of the second colored areas A2. The superposition area A4 is provided at an end at an opposite side of the non-colored area A3. As described above, the superposition area A4 and the non-colored area A3 are provided, so that it is possible to allow a color of one end for the second colored area A2 to be light while allowing a color of the other end to be deep, and to more three-dimensionally express the display elements through light and shade in the whole of the display elements.

A color colored on the package sheet, for example, may be configured to be suitable according to Commission Internationale de l'Eclairage L*a*b* color space (hereinafter, "CIELab") disclosed in Japanese Unexamined Patent Publication No. 2008-507385. The CIELab is a mathematical tristimulus color scale based on the CIE 1976 standard. The CIELab enables colors to be described quantitatively and precisely. The CIELab allows a color to be plotted in a three-dimensional space similar to the xyz space of Cartesian coordinates. The CIELab has colors from green to red on the original x-axis in the xyz space of the Cartesian coordinates. CIELab regards this axis as an a-axis. Negative a* values indicate green, and positive a* values indicate red. The CIELab has colors from blue to yellow on the original y-axis in the xyz space of the Cartesian coordinates. The CIELab regards this axis as a b-axis. Negative b* values indicate blue, and positive b* values indicate yellow. The CIELab has brightness on the original z-axis in the xyz space of the Cartesian coordinates. The CIELab regards this axis as an L-axis. The L*-axis ranges from 100 to 0, and the value of 100 indicates white while the value of 0 indicates black. An L* value of 50 indicates a mid-tone gray (provided a* and b* are all zero). Any color may be plotted in the CIELab according to the three values (L*, a*, b*).

The three-dimensional CIELab enables calculation of the three color components of saturation, hue, and brightness. The components of hue and saturation can be determined in the two-dimensional space including the a-axis and the b-axis. The saturation is the relative degree of saturation of the perceived color, and is determined by a distance from the origin when measured in the a*b* plane.

For example, a color with a*b* values of (10, 0) exhibits a lesser saturation than a color with a*b* values of (20, 0). The latter color is qualitatively perceived as being stronger in red than the former color. The hue is the relative red, yellow, green, and blue in a particular color. A radius can be created from the origin to any color within the two-dimensional a*b* space. The hue is an angle measured from 0° (the positive a*-axis) to the created radius. The hue can be any value in a range of 0° to 360°. The brightness is determined by the L* value, and the higher in value, the stronger in white, and the lower in value, the stronger in black.

The color difference ΔE, which is a difference between colors can be evaluated based on, for example, the following equation. $\Delta E=((\Delta L^*)^2+(\Delta a^*)^2+(\Delta b^*)^2)^{1/2}$, In the above equation, L denotes brightness, a* denotes a coordinate of a red-green axis, and b* denotes a coordinate of a yellow-blue axis. By measuring the color difference with respect to a reference color, it is possible to specify a first color and a second color printed on a packing sheet, for example.

For example, the color difference can be measured by the following method. Specifically, firstly, L*a*b* of white serving as reference color is measured using a color-difference meter (for example, CR-300 manufactured by Konica Minolta, Inc.). In the present embodiment, a C-light source (standard of Commission Internationale de l'Eclairage (CIE)) is used as a light source of the meter. A diameter of a measurement window of the meter is 10 mm. Further, a white reference plate (Y=92.0, x=0.3145, y=0.3198) serving as a reference color when the color difference is measured is used, where Y is a value indicating the brightness, and x and y are plane coordinates of the chromaticity.

Thereafter, the measured measurement values (L*a*b*) are set as reference colors. Next, a package sheet and the like (a color difference of which is measured) as a sample are mounted on the white reference plate, and then L*a*b* of a target color is measured. Thus, the color differences of the sample to be measured with respect to the reference colors can be calculated. When a color portion of a sample to be measured is smaller than the measurement window of the meter, a predetermined portion is cut off in advance, and is arranged on the white reference plate without to perform measurement without causing a gap or overlapping.

A color difference ΔE between the first color and the second color is preferable to be large in order to increase distinguishability of display elements, and specifically, is preferable to be equal to or more than 1. When the color difference between the first color and the second color is equal to or more than 1, a user is able to generally distinguish the first color from the second color. Moreover, preferably, the color difference ΔE between the first color and the second color is preferable to be equal to or more than 10. When the color difference between the first color and the second color is equal to or more than 10, a user is able to distinguish the first color from the second color more apparently, and display elements can be expressed more three-dimensionally by a combination of the first color and the second color.

The first color and the second color are preferable to be in a complementary color relation. In the present embodiment, the complementary color relation indicates a color with hue in the range of 180±45 degree. Preferably, in the case in which the hue is in the range of ±15 degree, a dark color may be more easily obtained when colors overlap each other. Specifically, for example, there are combinations of a green color for a red color, an orange color for a blue color, and a purple color for a yellow color.

An area of the superposition area A4 is preferable to be 1% to 50% relative to an area of the second colored area A2. The superposition area A4 in such a range is provided, so that the outline of the display elements are made to stand out and thus it is possible to clearly obtain a three-dimensional effect. Moreover, preferably, the area of the superposition area A4 is 10% to 33% relative to the area of the second colored area A2. Furthermore, an area of the non-colored area A3 is preferable to be 1% to 50% relative to the area of the second colored area A2. The non-colored area A3 in such a range is provided, so that it is possible to clearly obtain a three-dimensional effect of the display elements. Moreover, preferably, the area of the non-colored area A3 is 10% to 33% relative to the area of second colored area A2.

In the present embodiment, as illustrated in FIG. 4, the second color is arranged to overlap on the first color. At least the second color of the first color and the second color is configured to have light transmitting property. The second color has the light transmitting property, so that the second color and the first color which is a lower layer thereof can be seen as if they are mixed when the first color and the second color overlap each other. In addition, the brightness of the second color is configured to be lower than the brightness of the first color. The brightness of the second color is configured to be low, so that the second color and the first color which is a lower layer thereof can be easily seen as if they are mixed when the first color and the second color overlap each other.

The coloring of the package sheet 70 can be performed according to various well-known coloring technologies. The coloring includes printing, coating, and impregnation, but is not limited thereto. A printing method, for example, includes relief printing, flexo printing, gravure printing, offset printing, screen, and inkjet, but is not limited thereto.

The absorbent article 1 and the package sheet 70 are configured to be folded with the topsheet 10 of the absorbent article 1 disposed at the inner side thereof at a predetermined folding position along the widthwise direction W and the longitudinal direction L. Specifically, the package sheet 70 is folded through two longitudinal folding lines FL1 and FL2 along the longitudinal direction L, and is folded through transverse folding lines FW1 and FW2 along the widthwise direction W. The longitudinal folding lines and the transverse folding lines are indicated by dashed-dotted lines in FIG. 1 and FIG. 2. In the state in which the absorbent article 1 is folded, one end, in the longitudinal direction L, of the package sheet 70 adheres to the package sheet 70. The end of the package sheet 70 adheres to a part of the package sheet 70 by an adhesive tape 75. A material of the adhesive tape 75 is formed by a single layer film such as a polypropylene film or a polyethylene film, or a multi-layer film obtained by laminating a plurality of types of resin films.

Figure 6:
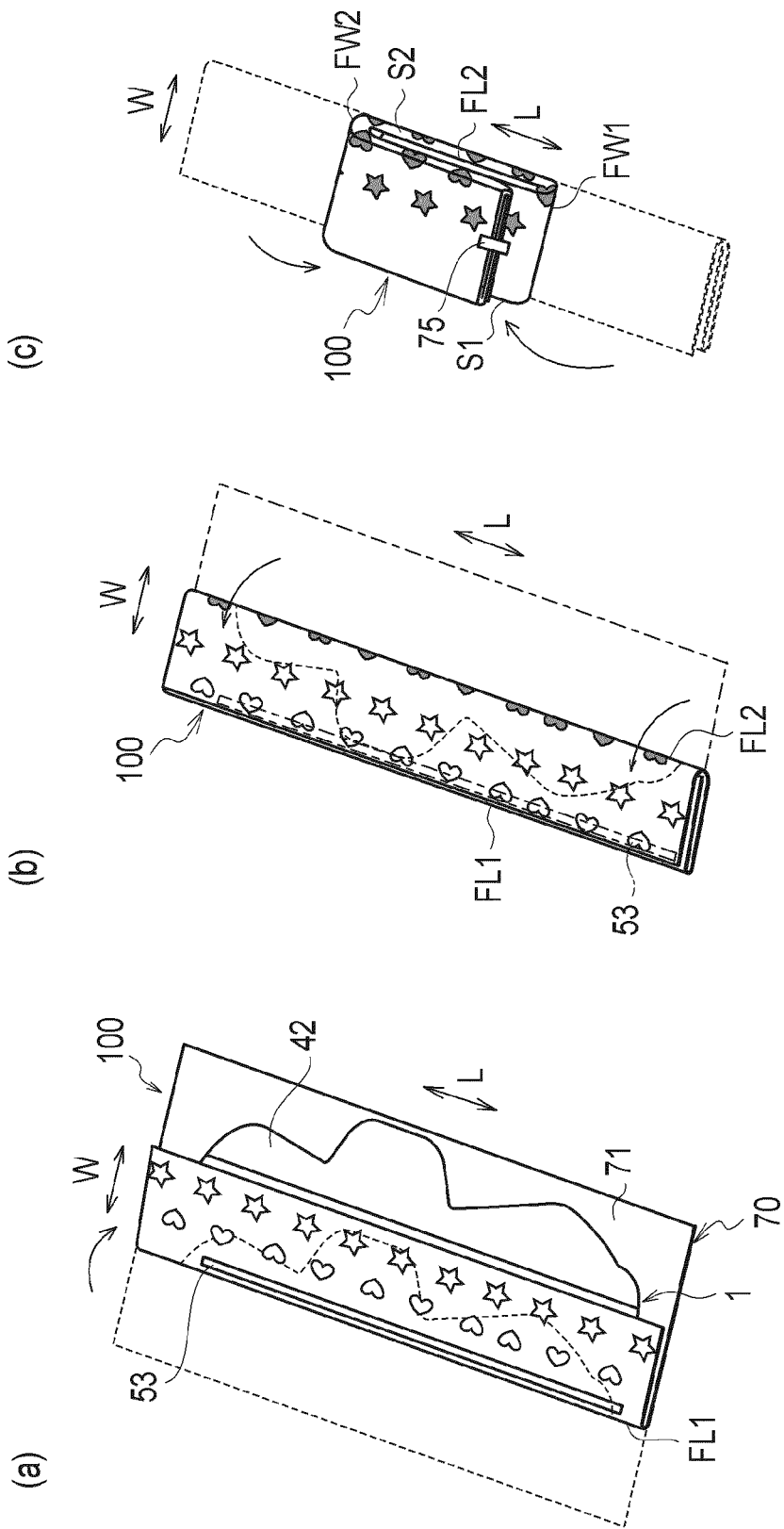
FIG. 6 is a perspective view schematically illustrating a folding process of the absorbent article package illustrated in FIG. 1.

Next, a method of folding the absorbent article package 100 will be described. FIG. 6 is a perspective view schematically illustrating a folding process of the absorbent article package 100. The folding process of the absorbent article package 100 includes an absorbent article mounting step, a first folding step, a second folding step, a bonding step, and a third folding step.

In the absorbent article mounting step, the absorbent article 1 is arranged on the package sheet 70. The package sheet 70 faces the backsheet 20 of the absorbent article 1. In addition, the absorbent article 1 may be arranged on the package sheet 70 dimensioned to individually package one absorbent article 1, or for example, a plurality of absorbent articles may be arranged on a package sheet, which is continuous along a conveyance direction, at a predetermined interval. In the present embodiment, for the purpose of convenience, a folding method will be described using an absorbent article package that packages one absorbent article.

In the first folding step, as illustrated in FIG. 6 (*a*), the package sheet 70 and the absorbent article 1 are folded inward about the first longitudinal folding line (see FIG. 1) FL1 along the longitudinal direction L from an end region side including one end side of the absorbent article 1 in the widthwise direction W. In the second folding step, as illustrated in FIG. 6 (*b*), the package sheet 70 and the absorbent article 1 are folded inward about the second transverse folding line FL2 (see FIG. 1) along the longitudinal direction L from an end region side including the other end side of the absorbent article 1 in the widthwise direction W.

Next, in the boding step, widthwise ends of the absorbent article 1 and the package sheet 70, which are folded back about the second longitudinal folding line FL2, adhere to the package sheet 70 through a hot melt-type adhesive member. Through the present step, the absorbent article 1 is individually packaged by the package sheet 70. It is sufficient if the hot melt-type adhesive member is arranged to allow a widthwise end of the rear surface 71 of the package sheet to adhere to the front surface 72 of the package sheet.

In addition, in the present embodiment, the widthwise end of the package sheet 70 folded back about the first longitudinal folding line FL1 and the second longitudinal folding line FL2 adheres through the hot melt-type adhesive member. However, the widthwise end of the package sheet 70 may not adhere. Furthermore, a method of adhering the widthwise end of the package sheet 70 may be performed by thermal welding, crimping, or ultrasonic welding.

In the third folding step, as illustrated in FIG. 6 (*c*), the package sheet 70 and the absorbent article 1 are folded inward about the first transverse folding line FW1 and the second transverse folding line FW2 (see FIG. 1) along the widthwise direction W from both end sides in the longitudinal direction L of the absorbent article 1. The aforementioned steps are performed, so that the absorbent article package 100 is folded to be small.

In addition, when the package sheet 70 and the absorbent article 1 are folded back from both end sides in the longitudinal direction L of the absorbent article 1, they may be configured to be folded back one by one from one end side in the longitudinal direction L, or they may be configured to be folded back at a time from both end sides in the longitudinal direction L.

As described above, the package sheet 70 and the absorbent article 1 are folded, so that the absorbent article 1 can be individually packaged by the package sheet 70 in a compact manner. Since the absorbent article 1 is miniaturized, when the absorbent article 1 is contained in a bag such as a makeup bag or a pochette, simple carrying is possible without occupying a large portion of a storage space of the bag. Furthermore, since the absorbent article 1 is individually packaged in a compact manner, when a user carries the absorbent article 1 in a toilet and the like at the time of use of the absorbent article 1, the user is able to arrange the absorbent article 1 in her hand even in a non-folded state and to hold the absorbent article 1 so as not to be seen by another person.

As illustrated in FIG. 3, the display element units 61 positioned at the widthwise center of the package sheet 70 are configured by the first non-colored areas A12, and are positioned between the first longitudinal folding line FL1 and the second longitudinal folding line. Furthermore, the display element units 61 positioned at both widthwise ends of the package sheet 70 are configured by the first non-colored areas A12 and the second colored areas A2, and are positioned at the widthwise outer side from the first longitudinal folding line FL1 or the widthwise outer side from second longitudinal folding line FL2.

Consequently, in the state in which the package sheet and the absorbent article are folded along the first longitudinal folding line or the second longitudinal folding line, display element units positioned at the widthwise outer side from the first longitudinal folding line and the second longitudinal folding line are seen. The display element units are configured by the first non-colored areas.

Meanwhile, in the state in which the package sheet and the absorbent article are folded along the transverse folding line, display element units positioned between the first longitudinal folding line in the widthwise direction and the longitudinal folding line are seen. The display element units are configured by the first non-colored areas and the second colored areas. That is, in the state in which the package sheet and the absorbent article are folded along the longitudinal folding line and in the state in which the package sheet and the absorbent article are folded along the transverse folding line, since the configurations of the display element units can be made to be different from each other, it is possible to increase a variation in a decoration mode.

The display element units 61 are provided on the first longitudinal folding line FL1 and the non-display element unit 62 is provided on the second longitudinal folding line FL2. The display element units 61 of the package sheet 70 are arranged over the first longitudinal folding line FL1 in the widthwise direction W, and are arranged over a first side portion S1, in which the first longitudinal folding line is arranged, of side portions of the package sheet 70 in the state in which the absorbent article 1 is packaged. Accordingly, in the folded state, display elements are imparted to the widthwise inner side and the widthwise outer side of the first side portion S1 (see FIG. 6), so that it is possible to obtain a sense of depth.

In addition, the non-display element unit 62 is arranged at a second side portion S2, in which the second longitudinal folding line is arranged, of the side portions of the package sheet in the state in which the absorbent article is packaged. Accordingly, in the folded state, decoration modes of the first side portion of the first longitudinal folding line side and the second side portion of the second longitudinal folding line side can be made to be different from each other, so that a user can see a different color or pattern of the absorbent article package depending on a user's viewing angle or a user's holding angle.

Next, a part of a method of manufacturing the absorbent article package according to the present embodiment will be described. As far as the method that is not described in the present embodiment is concerned, the existing method can be used. According to a method of manufacturing the absorbent article, the back surface 71 of the package sheet 70 is applied with the adhesive member 50. The adhesive member, for example, is a hot melt-type adhesive and has a property that it becomes soft by heat. The side of the backsheet 20 of the absorbent article 1 is stuck to come into contact with the adhesive member 50.

In addition, an adhesive member applied on the rear surface of the package sheet is configured to be soft in the state in which the adhesive member is applied on the backsheet. Accordingly, when the absorbent article 1 is stuck to the package sheet 70, if concave and convex portions are formed in the package sheet by embossing and the like as with the conventional art, the adhesive member applied on the rear surface of the package sheet is applied along the concave and convex portions. However, since the adhesive member is hardened according to passage of time, an air is included when the adhesive member adheres to the absorbent article. An adhesive member at the part, in which an air is included, remains in the package sheet side and may not be transferred to the absorbent article.

However, since the package sheet according to the present embodiment is not formed with concave and convex portions by embossing and the like, a contact surface with the adhesive member in the package sheet is smooth, so that it is possible to appropriately transfer the adhesive member, resulting in the suppression of the occurrence of a problem due to including an air. Furthermore, it is possible to ensure a contact area between the adhesive member of the absorbent article and the package sheet, and to suppress the reduction of adhesion of the adhesive member of the absorbent article. Since it is possible to suppress shift between the absorbent article and the package sheet, the adhesive member of the absorbent article before being used is difficult to be exposed.

Figure 7:
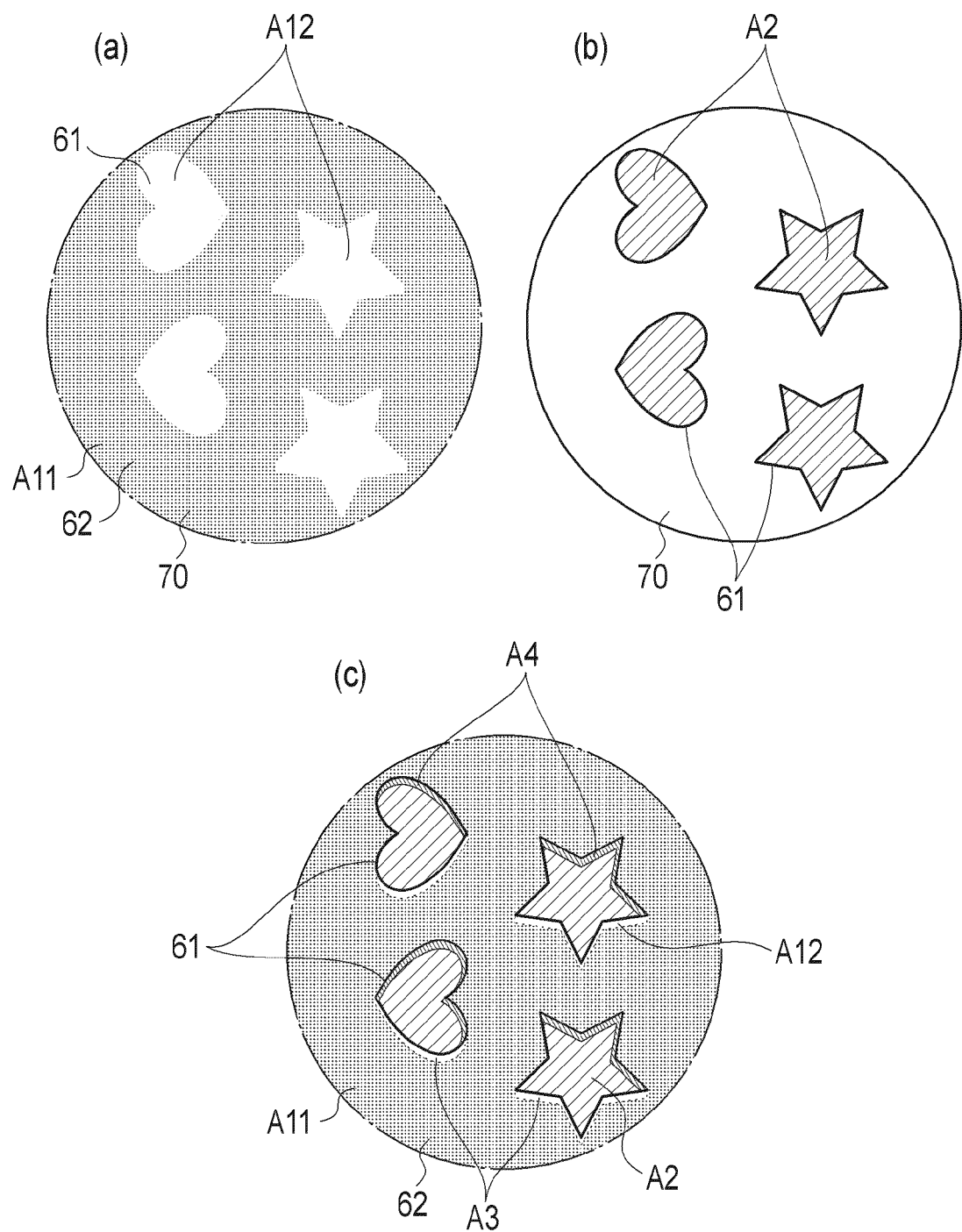
FIG. 7 is a schematic view for explaining a method of printing a package sheet.

Furthermore, a method of printing the package sheet may use the following method. FIG. 7 is a schematic diagram for explaining the printing method. Specifically, for example, the non-display element unit 62 of the package sheet is printed with the first color. FIG. 7 (*a*) illustrates the state in which the non-display element unit 62 is printed with the first color. The first colored area A11 printed with the first color constitutes the non-display element unit 62, and the first non-colored area A12 not printed with the first color constitutes the display element unit 61. The non-display element unit 62 is a whitened part and is indicated by a color of a base material of the package sheet 70. Next, the display element unit 61 is printed with the second color. FIG. 7 (*b*) illustrates the state in which the display element unit is printed with the second color with respect to the package sheet not printed with the first color. The display element unit 61 is configured by the second colored area A2 printed with the second color. FIG. 7 (*c*) illustrates the state in which the package sheet printed with the first color is printed with the second color.

When the first non-colored area A12 and the second colored area A2 have the same shape, the coloring is performed such that a partial shift is made, for example. In this way, the second colored area A2 printed with the second color constitutes the display element unit 61, the superposition area A4, in which the first color and the second color overlap each other, is arranged along the outline of the second colored area A2, and the non-colored area A3 not printed with the first color and the second color is arranged along the outline of the second colored area A2, so that it is possible to apply three-dimensional decoration.

When the first non-colored area A12 and the second colored area A2 have similar shapes, they are colored to overlap each other, for example. In this way, the display element unit 61 is configured by the second colored area A2 printed with the second color, and the superposition area A4, in which the first color and the second color overlap each other, is arranged along the outline of the second colored area A2, so that it is possible to apply three-dimensional decoration.

Furthermore, according to the three-dimensional decoration, the display element unit can be colored with the first color, and then can be colored with the second color along the outline of the display element unit colored with the first color. Moreover, a color for coloring the package sheet is not limited to two colors, and may be equal to or more than three colors.

The absorbent article package 100 is contained in the container bag 201. FIG. 8 is a perspective view illustrating an absorbent article container 200 in the state in which a plurality of absorbent article packages 100 are contained in the container bag 201. The container bag 201 has a bag shape for containing a plurality of absorbent article packages 100. The plurality of absorbent article packages 100 arranged in the transverse direction are contained in the container bag 201. Since an opening 202 is provided at the upper portion of the container bag 201, a wearer is able to take the absorbent article packages 100 in and out through the opening 202. In addition, it is sufficient if the opening 202 of the container bag 201 is configured such that the absorbent article 1 can be taken in and out of the bag 201, and the position and shape of the opening 202 are not limited to the example illustrated in FIG. 8.

The container bag 201 is printed with container bag display units 203 indicating display elements imparted to a package sheet. The container bag display unit 203 is configured by a combination of a star-shaped pattern and a heart-shaped pattern that are equal to those of the display elements printed on the package sheet 70. One side S3 of a plurality of sides of the container bag 201 is provided with a window unit 204 through which the absorbent article packages 100 contained in the container bag 201 are visible. The one side S3 described herein is a surface positioned at the front in FIG. 8, and the window unit 204 formed at the side is configured such that only the non-display element unit 62 of the package sheet constituting the absorbent article package 100 is visible. That is, when a user sees the container bag from the front side of FIG. 8, the window unit 204 is not configured such that the pattern and the like imparted to the package sheet 70 are seen through the window unit 204, and is configured such that a blank part, other than the pattern of the package sheet 70, is seen through the window unit 204.

In addition, in the present embodiment, among the sides of the container bag, at the side of the front side illustrated in FIG. 8 and the side positioned at the upper portion, window units through which the absorbent article package contained in the container bag is visible are formed. The absorbent article container according to the present invention has a concept that it may be configured such that only the non-display element units of the package sheet are visible through the window unit formed at least one side, it is sufficient if a container display unit is imparted to the one side, and it may be configured such that the display element units of the package sheet are visible through the window unit formed at the other side.

Furthermore, the sides include all sides of the container, and have a concept to include all surfaces including an upper surface positioned at an upper portion, a bottom surface positioned at a lower portion, a front surface positioned at a front side, a rear surface positioned at a rear side, a left side surface positioned at a left side, a right side surface positioned at a right side, and the like. In addition, it is sufficient if the window unit is configured such that the absorbent article package contained in the container is visible therethrough, and for example, it is sufficient if the window unit is transparent or semi-transparent.

Since the container bag display unit 203 is provided at the side having the window unit, it is possible to express decoration equal to that of the package sheet by the display elements in the container bag display unit 203 and the non-display element of the package sheet. A wearer is able to see the display element units and the non-display element unit from the outside of the container bag and understand the characteristic or usage such as the absorption performance and the like of the absorbent article 1 contained in the container bag. Consequently, a wearer is able to understand and select the performance of an absorbent article from the outside of the container bag 201 at the time of selection of the absorbent article.

In addition, the display element printed on the package sheet and the display element in the container bag display unit 203 may have the same shape or have similar shapes. Furthermore, the display element printed on the package sheet and the display element in the container bag display unit 203 may have the same color or have colors different from each other.

Since it is configured such that only the non-display element unit of the package sheet is visible through the window unit 204, it is possible to impart a character of a product name and the like of an absorbent article while overlapping the window unit 204. Even when an information display unit of a character and the like is imparted while overlapping the window unit 204, since the pattern and the character imparted to the package sheet 70 do not overlap each other, it is possible to suppress the reduction of visibility of the character and to indicate information by the character.

Since the display element unit 61 of the package sheet 70 is arranged over the first side portion S1, in which the first longitudinal folding line is arranged, of the side portions of the package sheet 70, the display element unit 61 is larger than a thickness dimension of the first side portion S1. Accordingly, in the state in which the side first portion of the package sheet is seen, it is difficult to understand the display element and to understand the content and the like of the display element. However, since a container bag display element including the display element of the package sheet is provided on the container bag, a user is able to see the display element indicated on the container bag and understand the content and the like of the display element.

The container bag 201 is formed with an auxiliary window unit 205 through which the display element units of the package sheet 70 constituting the absorbent article package 100 contained in the container bag 201 is visible. In the state in which the absorbent article package 100 is contained in the container bag 201, the display elements are visible through the auxiliary window unit 205, resulting in the improvement of the decoration property of the container. It is sufficient if the auxiliary window unit is configured such that at least a part of the display elements unit are visible therethrough. In addition, in the present embodiment, the auxiliary window unit is formed on a surface adjacent to the surface on which the window unit is formed in the container bag. However, the present invention is not limited to this configuration. The auxiliary window unit may be formed on the surface on which the window unit is formed, or a surface facing the surface on which the window unit is formed.

In addition, the display element may be three-dimensionally displayed by a combination of the first color and the second color, or by one color such as only the first color or only the second color. For example, the whole of the package sheet is printed with the first color and the display element is further printed with the second color thereon. It is configured such that only the first color of the package sheet is visible through the window unit of the storage bag, and the display element is printed with the second color on the surface on which the window unit of the storage bag is formed. Even in such a configuration, it is possible to apply decoration equal to that of the package sheet 70 by the display element of the second color printed on the surface on which the window unit 204 of the container bag 201 is provided and the non-display element unit of the first color which is visible through the window unit. That is, in the state in which a plurality of the absorbent article packages 100 are contained in the container bag 201, it is possible to indicate the characteristic or usage of the absorbent article with respect to a user.

In the present embodiment, only the front surface (a surface positioned at an outer side when the absorbent article is packaged) of the package sheet is printed. However, only the rear surface (a surface positioned at an inner side when the absorbent article is packaged) of the package sheet may be printed, or the front surface and the rear surface of the package sheet may be printed. In the present embodiment, the first non-colored area and the second colored area are configured to have the same shape. However, the first non-colored area and the second colored area may have similar shapes, or the first non-colored area and the second colored area may have analogous shapes. The analogous shape, for example, includes a true circular shape and an elliptical shape.

In the present embodiment, the adhesive member provided on the backsheet of the absorbent article is configured to come into contact with the package sheet. However, it may be configured such that a release sheet may be provided between the package sheet and the adhesive member, and an adhering area is covered by the release sheet. The release sheet, for example, may be formed by a nonwoven material, a film, a paper, a laminate, and/or a cloth (including a woven cloth) material, and a combination of these materials.

As the absorbent article, a plurality of absorbent articles having different absorption performance may be prepared, and it may be configured such that the performance and the like of the absorbent article are indicated by the display elements and the like. For example, as the absorbent article package, a first absorbent article package having a first absorbent article with first absorption performance, a first container bag that contains the first absorbent article package, a second absorbent article package having a second absorbent article with second absorption performance different from the first absorption performance, and a second container bag that contains the second absorbent article package are provided, and a first display element indicating the first absorption performance and a second display element indicating the second absorption performance are provided.

For example, the first absorbent article is a sanitary napkin in daytime and the second absorbent article is a sanitary napkin at night. A display element unit of the first absorbent article is configured to have the first display element indicating the first absorption performance, and a display element unit of the second absorbent article is configured to have the second display element indicating the second absorption performance. For example, the first display element may be a floral pattern unit that reminds a daytime image, and the second display element may be a star pattern unit that reminds a night image.

The container bag includes the first container bag that contains the first absorbent article and the second container bag that contains the second absorbent article, a first container bag display unit indicating the first display element is provided on a surface on which a window unit of the first container bag is formed, and a second container bag display unit indicating the second printing element is provided on a surface on which a window unit of the second container bag is formed.

A wearer is able to see the first display element unit or the second display element unit from the outside of the container bag, and understand the absorption performance of the absorbent article 1 contained in the container bag. Consequently, a wearer is able to understand and select the performance of an absorbent article from the outside of the container bag 201 at the time of selection of the absorbent article. The display element is configured by a pattern and/or a mark. However, it may be configured such that the absorption performance is indicated by the content and the number of the display elements. Consequently, a wearer is able to intuitively understand absorption performance as compared with the case in which absorption performance is indicated by a character and the like.

Moreover, for example, as a pattern that reminds a daytime or bright image, a solar pattern or a heart-shaped pattern is available as well as the floral pattern. Display elements having such patterns are used, so that it is possible to inform a wearer that it is a sanitary napkin in daytime, or a sanitary napkin for a day in which menses is light (a physiological amount is small). Meanwhile, as a pattern that reminds a night image, a moon pattern is available as well as the star-shaped pattern. Such display elements are used, so that it is possible to inform a wearer that it is a sanitary napkin at night, or a sanitary napkin for a day in which menses is heavy (a physiological amount is large).

Furthermore, according to the configuration in which the absorption performance of the absorbent article is indicated by the patterns of the display elements, it is possible to obtain a decoration effect based on a pattern and the like and to prettily decorate the absorbent article, as compared with the configuration in which the characteristic of the absorbent article is instructed to a wearer by a character and the like. Moreover, since an index at the time of selection of the absorbent article is a pattern, a wearer is able to enjoyably select the absorbent article by the appearance without being conscious of a gloomy feeling of menses at the time of selection.

In addition, the color imparted to the first absorbent article package and the color imparted to the second absorbent article package may be equal to each other or colors different from each other. The performance and the like of the absorbent article may be configured to be indicated by a difference between colors to be colored. For example, it may be configured such that the package sheet for packaging the first absorbent article may be colored with the first color and the second color, the package sheet for packaging the second absorbent article may be colored with a third color and a fourth color, or it may be configured such that the package sheet for packaging the first absorbent article may be colored with the first color and the second color and the package sheet for packaging the second absorbent article may be colored with the first color and the third color. In addition, when the color imparted to the first absorbent article package and the color imparted to the second absorbent article package are equal to each other, the performance and the like of the absorbent article are configured to be indicated by the pattern of the display element.

Figure 9:
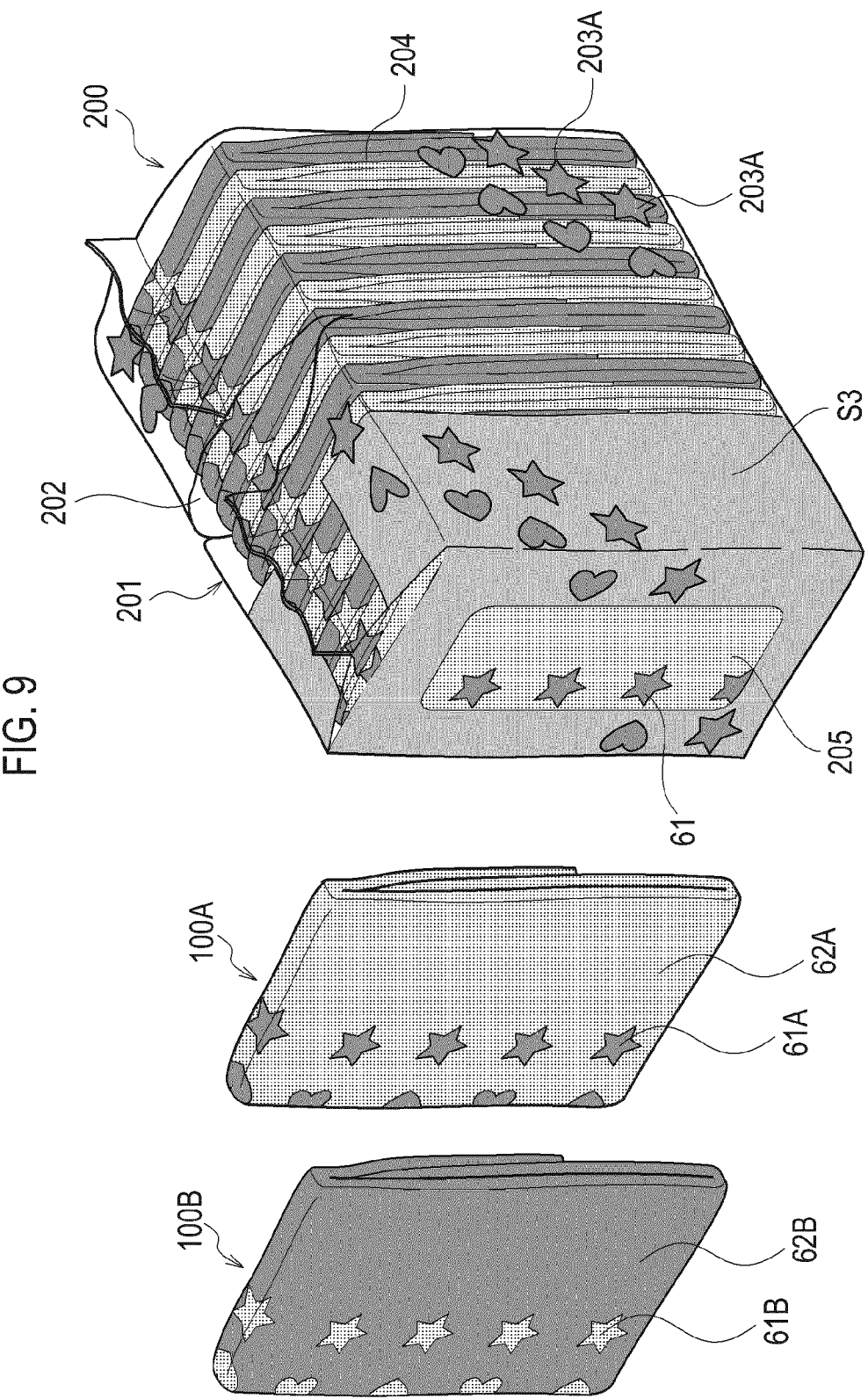
FIG. 9 is a perspective view of an absorbent article container according to a modification.

Next, an absorbent article container 200A according to a modification will be described on the basis of FIG. 9 and FIG. 10. The absorbent article container 200A according to the modification includes a first colored pattern package 100A colored with a first colored pattern and a second colored pattern package 100B colored with a second colored pattern different from the first colored pattern as absorbent article packages, and contains these packages. The first colored pattern package 100A and the second colored pattern package 100B are absorbent article packages with the same absorption performance, and the colored patterns of package sheets thereof are different from each other.

A display element unit 61A of the first colored pattern package 100A and a non-display element unit 62B of the second colored pattern package 100B are colored with the same color, and a display element unit 61B of the second colored pattern package 100B and a non-display element unit 62A of the first colored pattern package 100A are colored with the same color. In the container bag 201, the first colored pattern packages 100A and the second colored pattern packages 100B are alternately arranged. A container bag display unit 203A is arranged at one side S3 of the container bag, and is colored with the same color as that of the display element unit 61A of the first colored pattern package.

According to the absorbent article container 200A configured as above, it is possible to express decoration the same as that of the package sheet by a display element in the container bag display unit 203A and a display element unit of the package sheet. A wearer is able to see the display element unit and the like from the outside of the container bag, and to understand the characteristic or usage such as the absorption performance and the like of the absorbent article 1 contained in the container bag.

Moreover, the colored patterns of the first colored pattern package 100A and the second colored pattern package 100B with the same absorption performance are made to be different from each other, so that it is possible to improve decoration property. Furthermore, the display element unit 61A of the first colored pattern package 100A and the non-display element unit 62B of the second colored pattern package 100B are colored with the same color, and the display element unit 61B of the second colored pattern package 100B and the non-display element unit 62B of the first colored pattern package 100A are colored with the same color, wherein they are colored with two colors. Consequently, it is possible to increase a variation in the absorbent article package without an increase in the number of colors.

In an absorbent article package with absorption performance different from that of the absorbent article package according to the modification, the first colored pattern package 100A and the second colored pattern package 100B are colored with two colors different from each other, and are used as a third colored pattern package and a fourth colored pattern package, so that it is possible to increase a variation. For example, an absorbent article package in daytime is colored with two colors of a pink color and a green color and an absorbent article package at night is colored with two colors of a purple color and a yellow color, so that it is possible to indicate a difference in absorption performance by a combination of the colors.

In addition, the absorbent article package according to the modification, for example, may be manufactured by the following method. According to a method of manufacturing absorbent articles, the absorbent articles may be manufactured by a well-known method and are arranged on a continuous package sheet. FIG. 10 illustrates the state in which absorbent articles are arranged on the package sheet. A plurality of absorbent articles are arranged at an interval in a conveyance direction of the package sheet.

Although not illustrated in the drawing, in the state illustrated in FIG. 10, the absorbent articles and the package sheet are folded along the conveyance direction and then are cut into a product length, so that individual absorbent article packages are manufactured. CL illustrated in FIG. 10 virtually indicates a cutting line of the package sheet.

On the package sheet 70, first colored patterns and second colored patterns are alternately printed in the conveyance direction. The lengths in the conveyance direction of each first colored pattern and each second colored pattern are the product length of the package sheet. For example, FIG. 10 (*a*) illustrates the state in which the boundary between the first colored pattern and the second colored pattern coincides with the cutting line CL. According to a manufacturing method illustrated in FIG. 10 (*a*), the first colored pattern package 100A with the first colored pattern and the second colored pattern package 100B with the second colored pattern can be continuously and alternately manufactured.

Furthermore, in FIG. 10 (*b*), the boundary between the first colored pattern and the second colored pattern is arranged to be shifted from the cutting line CL. The rear side end of each absorbent article package has partially different colored pattern. As described above, since the rear side end of the absorbent article package has the different colored pattern, the rear side end of the absorbent article package, that is, rear end of the package sheet is easily noticeable. The rear end of the package sheet is a portion grasped in the state, in which the package sheet is deployed about the second transverse folding line FW2 (see FIG. 1), when the absorbent article package is opened. The rear end of the package sheet is made to stand out, so that a wearer is able to easily understand a portion to be grasped and easily open it.

In FIG. 10 (*c*), the boundary between the first colored pattern and the second colored pattern is arranged to be shifted from the cutting line CL. The front side end of each absorbent article package has partially different colored pattern. FIG. 10 (*d*) is a diagram illustrating the second colored pattern package 100B manufactured by the arrangement pattern of FIG. 10 (*c*).

In the first colored pattern package 100A and the second colored pattern package 100B manufactured by the arrangement pattern of FIG. 10 (*c*), since the front side end of the absorbent article package has the partially different colored pattern, the front side end of the absorbent article package, that is, a front end 70F of the package sheet is easily noticeable. The front end 70F of the package sheet is a portion to which the adhesive tape 75 adheres in the state in which the package sheet is folded. In the case of opening the absorbent article package in the state illustrated in FIG. 10 (*d*), the adhesive tape 75 or the front end 70F of the package sheet is grasped and the package sheet 70 is opened. Accordingly, the front end 70F of the package sheet 70 is made to stand out, so that a wearer is able to easily understand a portion to be grasped and easily open it.

In addition, the first colored pattern package 100A and the second colored pattern package 100B according to the present embodiment have a concept that more than half of the area of the package sheet is the first colored pattern and a part thereof is the first colored pattern package 100A with the second colored pattern, or more than half of the area of the package sheet is the second colored pattern and a part thereof is the second colored pattern package 100B with the first colored pattern.

Moreover, the color of the package sheet itself is made to change, so that it is possible to increase a variation in a decoration pattern. Furthermore, the performance and the like of the absorbent articles may be configured to be indicated by allowing the colors of the package sheet for surrounding the first absorbent article and the package sheet for surrounding the second absorbent article to be different from each other.

The entire contents of Japanese Patent Application No. 2011-112926 (filed on May 19, 2011) and Japanese Patent Application No. 2012-065222 (filed on Mar. 22, 2012) are incorporated in the present specification by way of reference.

INDUSTRIAL APPLICABILITY

A display element unit having a display element is imparted to a package sheet for surrounding an absorbent article, and a container bag display unit indicating the display element imparted to the package sheet is imparted to a container bag. The container bag is provided at one side with a window unit through which a package sheet of the absorbent article contained in the container bag is visible, and it is configured such that only a non-display element unit having no display element is visible through the window unit. Since the container bag display unit is provided at the one side provided with the window unit, it is possible to express decoration equal to that of the package sheet by the display element of the container bag display unit and the non-display element unit of the package sheet. It is possible to provide an absorbent article container in which a wearer is able to see the display element unit and the non-display element unit from the outside of the container bag, and to understand the characteristic or usage such as the absorption performance and the like of the absorbent article contained in the container bag.

REFERENCE SIGNS LIST

A11 . . . first colored area, A12 . . . first non-colored area, A2 . . . second colored area, A3 . . . non-colored area, A4 . . . superposition area, L . . . longitudinal direction, W . . . widthwise direction, 1 . . . absorbent article, 10 . . . topsheet, 20 . . . backsheet, 30 . . . absorber, 31 . . . lower layer absorber, 32 . . . upper layer absorber, 41, 42 . . . sidesheet, 43, 44 . . . wing unit, 50 . . . adhesive, 61 . . . display element unit, 62 . . . non-display element unit 70 . . . package sheet, 70F . . . front end of package sheet, 71 rear surface, 72 . . . front surface, 75 . . . adhesive tape, 100 . . . package, 100A . . . first colored pattern package, 100B . . . second colored pattern package, 200 . . . container, 201 . . . container bag, 202 . . . opening, 203 . . . container bag display unit, 204 . . . window unit, 205 . . . auxiliary window unit

The invention claimed is:

1. An absorbent article container including an absorbent article having a liquid-permeable topsheet, a liquid-impermeable backsheet, and an absorber arranged between the topsheet and the backsheet, a package sheet that individually packages the absorbent article,
   an absorbent article package in which the package sheet and the absorbent article are folded in a state in which the absorbent article has been arranged on the package sheet and the absorbent article is individually packaged by the package sheet, and a container bag that contains a plurality of the absorbent article packages, wherein
   the package sheet is provided with a display element unit having a display element indicating at least one of a pattern and a mark and a non-display element unit having no display element,
   the container bag is provided at one side with a window unit through which the absorbent article package contained in the container bag is visible,
   only the non-display element unit of the package sheet is configured to be visible through the window unit, and
   a container bag display unit indicating the display element is provided at the one side provided with the window unit of the container bag,
   wherein
   the display element unit is composed of a first color area colored with a first color,
   the non-display element unit is composed of a second color area colored with a second color,
   a non-colored area and a superimposition area in which the first color and the second color overlap each other are arranged along an outline of the first color area.

2. The absorbent article container according to claim 1, wherein
   the display element unit is provided at a first side portion of side portions of the package sheet in a state in which the absorbent article has been packaged,
   the non-display element unit is provided at a second side portion of the side portions of the package sheet, and
   the display element of the package sheet is larger than a thickness dimension of the first side portion.

3. The absorbent article container according to claim 2, wherein the second side portion of the package sheet is configured to be visible through the window unit.

4. The absorbent article container according to claim 2, wherein
   the absorbent article and the package sheet are configured to be folded inward from an outer side of the absorbent article about a first longitudinal folding line and a second longitudinal folding line along a longitudinal direction of the absorbent article,
   the first longitudinal folding line is arranged at the first side portion,
   the second longitudinal folding line is arranged at the second side portion, and
   the display element unit is provided over the first side portion in a widthwise direction of the absorbent article.

5. The absorbent article container according to claim 1, wherein the container is provided with an auxiliary window unit through which the display element unit of the package sheet is visible.

6. The absorbent article container according to claim 1, wherein the container bag display unit is colored with the first color.

7. The absorbent article container according to claim 1, wherein
   the absorbent article package comprises: a first absorbent article package having a first absorbent article with first absorption performance; and a second absorbent article package having a second absorbent article with second absorption performance different from the first absorption performance;
   the display element unit of the first absorbent article package has a first display element indicating the first absorption performance,
   the display element unit of the second absorbent article package has a second display element indicating the second absorption performance,
   the container bag comprises: a first container bag that contains the first absorbent article package; and a second container bag that contains the second absorbent article package,
   a first container bag display unit indicating the first display element is provided at one side on which the window unit of the first container bag has been formed, and a second container bag display unit indicating the second printing element is provided at one side on which the window unit of the second container bag has been formed.

8. The absorbent article container according to claim 1, wherein
   the absorbent article package comprises: a first colored pattern package colored with a first colored pattern; and a second colored pattern package colored with a second colored pattern different from the first colored pattern, wherein a display element unit of the first colored pattern package and a non-display element unit of the second colored pattern package are colored with the same color, a display element unit of the second colored pattern package and a non-display element unit of the first colored pattern package are colored with the same color, the first colored pattern packages and the second colored pattern packages are alternately arranged in the container bag, and the container bag display unit is colored with a color of one of the display element unit of the first colored pattern package and the display element unit of the second colored pattern package.

9. The absorbent article container according to claim 3, wherein the absorbent article and the package sheet are configured to be folded inward from an outer side of the absorbent article about a first longitudinal folding line and a second longitudinal folding line along a longitudinal direction of the absorbent article, the first longitudinal folding line is arranged at the first side portion, the second longitudinal folding line is arranged at the second side portion, and the display element unit is provided over the first side portion in a widthwise direction of the absorbent article.

10. The absorbent article container according to claim 2, wherein the container is provided with an auxiliary window unit through which the display element unit of the package sheet is visible.

11. The absorbent article container according to claim 3, wherein the container is provided with an auxiliary window unit through which the display element unit of the package sheet is visible.

12. The absorbent article container according to claim 4, wherein the container is provided with an auxiliary window unit through which the display element unit of the package sheet is visible.

13. The absorbent article container according to claim 9, wherein the container is provided with an auxiliary window unit through which the display element unit of the package sheet is visible.

14. The absorbent article container according to claim 2, wherein the container bag display unit is colored with the first color.

15. The absorbent article container according to claim 3, wherein the container bag display unit is colored with the first color.

16. The absorbent article container according to claim 4, wherein the container bag display unit is colored with the first color.

17. The absorbent article container according to claim 9, wherein the container bag display unit is colored with the first color.

18. The absorbent article container according to claim 5, wherein the container bag display unit is colored with the first color.

19. The absorbent article container according to claim 10, wherein the container bag display unit is colored with the first color.

20. The absorbent article container according to claim 11, wherein the container bag display unit is colored with the first color.

* * * * *